United States Patent [19]

Ramsay et al.

[11] Patent Number: 4,918,098

[45] Date of Patent: Apr. 17, 1990

[54] MACROLIDE COMPOUNDS

[75] Inventors: Michael V. J. Ramsay, South Harrow; Edward P. Tiley, Pinner; Oswy Z. Pereira, Hounslow; John B. Ward, Bushey; Neil Porter, Pinner; Hazel M. Noble, Slough; Richard A. Fletton, Ruislip; David Noble, Slough; Derek R. Sutherland, Chalfont St Giles, all of England

[73] Assignee: American Cyanamid Company, Stamford, Conn.

[21] Appl. No.: 24,763

[22] Filed: Mar. 11, 1987

[30] Foreign Application Priority Data

Mar. 12, 1986 [GB] United Kingdom ............... 8606122
Jun. 17, 1986 [GB] United Kingdom ............... 8614689
Jul. 4, 1986 [GB] United Kingdom ............... 8616346

[51] Int. Cl.$^4$ .................................. A61K 31/365
[52] U.S. Cl. ............................ 514/450; 549/218; 549/264
[58] Field of Search ............... 549/264, 218; 514/450

[56] References Cited

U.S. PATENT DOCUMENTS

| | | | |
|---|---|---|---|
| 4,201,861 | 5/1980 | Mrozik et al. | 536/7.1 |
| 4,423,209 | 12/1983 | Mrozik | 549/264 |
| 4,469,682 | 9/1984 | Mrozik | 549/264 |
| 4,587,247 | 5/1986 | Linn et al. | 549/264 |
| 4,696,945 | 9/1987 | Frei et al. | 549/264 |

FOREIGN PATENT DOCUMENTS

| | | | |
|---|---|---|---|
| 170006 | 2/1986 | European Pat. Off. | |
| 20284 | 2/1984 | Japan | 549/264 |
| 2166436A | 5/1986 | United Kingdom. | |
| 2176182A | 12/1986 | United Kingdom. | |

OTHER PUBLICATIONS

Theodora W. Greene, Protective Groups in Organic Synthesis, (1981), pp. 10–12.

*Primary Examiner*—Richard L. Raymond
*Assistant Examiner*—Amelia A. Owens
*Attorney, Agent, or Firm*—Bacon & Thomas

[57] ABSTRACT

Compounds are described of formula (I)

and salts thereof, wherein
$R^1$ a methyl, ethyl or isopropyl group;
$R^2$ is —H, —OH, substituted —OH or a phosphate ester group and $R^3$ is —H, or $R^2$ and $R^3$ together with the carbon atom to which they are attached represent a >C=O group
and $OR^4$ is a group $OR^5$ as defined above;

with the proviso that either $R^2$ represents a group $OR^5$ (where $OR^5$ is an alkoxy group $OR^7$ in which $R^7$ represents a $C_{1-6}$ alkyl substituted by a halogen atom or $C_{2-6}$ alkyl interrupted by —O— or —S—) or at least one of $R^2$ and $OR^4$ is a phosphate ester group or a group $OCONR^{10}R^{11}$ (where $R^{10}$ and $R^{11}$ are —H or $C_{1-4}$ alkyl).

These compounds may be used for controlling insect, acarine, nematode or other pests.

12 Claims, No Drawings

MACROLIDE COMPOUNDS

This invention relates to novel antibiotic compounds and to processes for their preparation.

In our United Kingdom Patent Specification No. 2166436A we describe the production of Antibiotics S541 which may be isolated from the fermentation products of a novel Streptomyces sp.

We have now found a further group of compounds with antibiotic activity which may be prepared by chemical modification of Antibiotics S541. The novel compounds of the invention have antibiotic activity and/or are of use as intermediates in the preparation of other active compounds.

Thus, in one aspect, the invention particularly provides the compounds of formula (I)

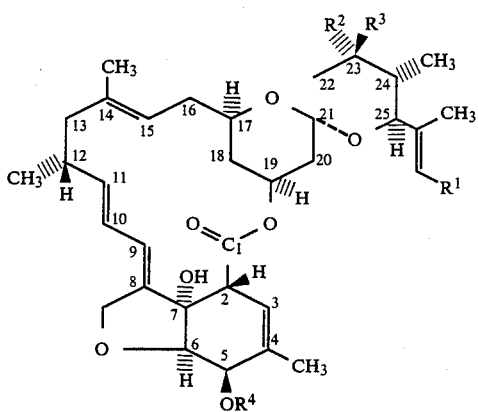

and salts thereof, wherein $R^1$ represents a methyl, ethyl or isopropyl group; $R^2$ represents a hydrogen atom or a group $OR^5$ (where $OR^5$ is a hydroxyl group, a substituted hydroxyl group having up to 25 carbon atoms or a phosphate ester group) and $R^3$ represents a hydrogen atom, or $R^2$ and $R^3$ together with the carbon atom to which they are attached represent a $>C=O$ group; and $OR^4$ represents a group $OR^5$ as defined above; with the proviso that unless $R^2$ represents a group $OR^5$ where $OR^5$ is an alkoxy group $OR^7$ in which $R^7$ represents a $C_{1-6}$ alkyl group substituted by a halogen atom or a $C_{2-6}$ alkyl group interrupted by an oxygen or sulphur atom at least one of $R^2$ and $OR^4$ must represent a phosphate ester group or a group $OCONR^{10}R^{11}$ as defined below. When the compounds of formula (I) are to be used as intermediates $—OR^4$ will often be a protected hydroxy group and the invention particularly includes such protected compounds.

Where $R^2$ and/or $OR^4$ are phosphate ester groups, they may be for example groups of the formulae $—OP(O)(OH)_2$, $—OP(O)(OH)(OZ)$, $—OP(O)(OZ)_2$ or $—OP(O)(OCH_2CCl_3)_2$ where Z represents an alkali metal such as sodium or potassium.

When the group $R^2$ or $OR^4$ in compounds of formula (I) is a substituted hydroxyl group it may represent an acyloxy group [e.g. a group of the formula $—OCOR^6$, $—OCO_2R^6$ or $—OCSOR^6$ (where $R^6$ is an aliphatic, araliphatic or aromatic group, for example an alkyl, alkenyl, alkynyl, cycloalkyl, aralkyl or aryl group)], a formyloxy group, a group $—OR^7$ (where $R^7$ is as defined above for $R^6$), a group $—OSO_2R^8$ (where $R^8$ is a $C_{1-4}$ alkyl or $C_{6-10}$ aryl group), a silyloxy group, a cyclic or acyclic acetaloxy group, a group $OCO(CH_2)_nCO_2R^9$ (where $R^9$ is a hydrogen atom or a group as defined for $R^6$ above and n represents zero, 1 or 2) or a group $OCONR^{10}R^{11}$ (where $R^{10}$ and $R^{11}$ may each independently represent a hydrogen atom or a $C_{1-4}$ alkyl group e.g. methyl).

Where $R^6$ or $R^7$ are alkyl groups, they may be for example $C_{1-8}$ alkyl groups e.g. methyl, ethyl, n-propyl, i-propyl, n-butyl, i-butyl, t-butyl or n-heptyl which alkyl groups may also be substituted. Where $R^6$ is a substituted alkyl group it may be substituted by, for example, one or more, e.g. two or three halogen atoms (e.g. chlorine or bromine atoms), or a carboxy, $C_{1-4}$ alkoxy (e.g. methoxy, ethoxy), phenoxy or silyloxy group. Where $R^7$ is a substituted alkyl group it may be substituted by a cycloalkyl e.g. cyclopropyl group. $R^7$ may also represent a $C_{1-6}$ alkyl group substituted by a halogen (e.g. fluorine, chlorine, bromine or iodine) atom or a $C_{2-6}$ alkyl group interrupted by an oxygen or sulphur atom.

Where $R^6$ or $R^7$ are alkenyl or alkynyl groups, they may be for example $C_{2-8}$ alkenyl, e.g. allyl, or $C_{2-8}$ alkynyl groups.

Where $R^6$ or $R^7$ are cycloalkyl groups, they may be for example $C_{3-12}$ cycloalkyl, such as $C_{3-7}$ cycloalkyl, e.g. cyclopentyl groups.

Where $R^6$ or $R^7$ are aralkyl groups, they preferably have 1 to 6 carbon atoms in the alkyl moiety and the aryl group(s) may be carbocyclic or heterocyclic and preferably contain 4–15 carbon atoms e.g. phenyl. Examples of such groups include phen$C_{1-6}$alkyl, e.g. benzyl groups.

Where $R^6$ or $R^7$ are aryl groups, they may be carbocyclic or heterocyclic and preferably have 4–15 carbon atoms, and may be for example a phenyl group.

When $R^7$ in the compounds of formula (I) is a $C_{1-6}$ alkyl group substituted by a halogen atom it may be for example a halomethyl, haloethyl or halopropyl group.

When $R^7$ is a $C_{2-6}$ alkyl group interrupted by an oxygen or sulphur atom it may be for example a methoxymethyl, ethoxyethyl or methythiomethyl group.

When $R^2$ or $—OR^4$ is a group $—OSO_2R^8$, it may be for example a methylsulphonyloxy or p-toluenesulphonyloxy group.

Where $R^2$ or $—OR^4$ represents a cyclic acetaloxy group, it may for example have 5–7 ring members and may be for example a tetrahydropyranyloxy group.

When $R^2$ or $—OR^4$ represents a silyloxy group or $R^6$ contains a silyloxy substituent, the silyl group may carry three groups which may be the same or different, selected from alkyl, alkenyl, alkoxy, cycloalkyl, aralkyl, aryl and aryloxy groups. Such groups may be as defined above for $R^6$ and particularly include methyl, t-butyl and phenyl groups. Particular examples of such silyloxy groups are trimethylsilyloxy and t-butyldimethylsilyloxy.

Where $R^2$ and $OR^4$ represents a group $OCO(CH_2)_nCO_2R^9$, it may for example be a group $OCOCO_2R^9$ or $OCOCH_2CH_2CO_2R^9$ where $R^9$ represents a hydrogen atom or a $C_{1-4}$ alkyl (e.g. methyl or ethyl) group.

Salts that may be formed with compounds of formula (I) containing an acidic group include alkali metal salts such as sodium and potassium salts.

In the compounds of formula (I), the group $R^1$ is preferably an isopropyl group.

When $R^2$ and/or $OR^4$ in the compounds of formula (I) are phosphate esters, those compounds in which $R^2$ and/or $OR^4$ have the formula $—OP(O)(OH)_2$, $—OP(O)(OH)(OZ)$ or $—OP(O)(OZ)_2$ are preferred.

When OR$^4$ is a substituted hydroxyl group, preferred compounds of formula (I) are those in which OR$^4$ is a methoxycarbonyloxy or, especially, an acetoxy group. However, in general, compounds of formula (I) in which OR$^4$ is a hydroxy group are preferred.

Important compounds according to the invention are those of formula (I) in which R$^1$ is an ispropyl group, R$^2$ is a methoxymethoxy, methylthiomethoxy or ethoxyethoxy group, R$^3$ is a hydrogen atom and OR$^4$ is a hydroxy, acetoxy or methoxycarbonyloxy group.

Further important compounds according to the invention are those of formula (I) in which R$^1$ is an isopropyl group, R$^2$ is a 3-halopropoxy group, R$^3$ is a hydrogen atom and OR$^4$ is a hydroxy, acetoxy or methoxycarbonyloxy group.

Another group of important compounds according to the invention are those of formula (I) in which R$^1$ is an isopropyl group, R$^2$ is a group OCONR$^{10}$R$^{11}$ (where R$^{10}$ and R$^{11}$ may each independantly represent a hydrogen atom or a methyl group), R$^3$ is a hydrogen atom and OR$^4$ is a hydroxy, acetoxy or methoxycarbonyloxy group.

Yet another group of important compounds according to the invention are those of formula (I) in which R$^1$ is an isopropyl group, R$^2$ is a hydroxy group, R$^3$ is a hydrogen atom and OR$^4$ us a group OP(O)(OH)$_2$, OP(O)(OH)(ONa) or OP(O)(ONa)$_2$.

An important active compound of the invention is that of formula (I) in which:

R$^1$ is an isopropyl group, R$^2$ is a methoxymethoxy group, R$^3$ is a hydrogen atom and OR$^4$ is a hydroxy group.

Another important active compound of the invention is that of formula (I) in which:

R$^1$ is an isopropyl group, R$^2$ is a methylthiomethoxy group, R$^3$ is a hydrogen atom and OR$^4$ is a hydroxy group.

Another important active compound of the invention is that of formula (I) in which:

R$^1$ is an isopropyl group, R$^2$ is a 3-chloropropoxy group, R$^3$ is a hydrogen atom and OR$^4$ is a hydroxy group.

Another important active compound of the invention is that of formula (I) in which:

R$^1$ is an isopropyl group, R$^2$ is an N-methylaminocarbonyloxy group, R$^3$ is a hydrogen atom and OR$^4$ is a hydroxy group.

As indicated previously, the compounds according to the invention may be of use as antibiotics and/or as intermediates for the preparation of other active compounds. When the compounds of the invention are to be used as intermediates, the R$^2$ or —OR$^4$ groups may be a protected hydroxyl group. It will be appreciated that such a group should have the minimum of additional functionality to avoid further sites of reaction and should be such that it is possible to selectively regenerate a hydroxyl group from it. Examples of protected hydroxyl groups are well known and are described, for example, in "Protective Groups in Organic Synthesis" by Theodora W. Greene. (Wiley-Interscience, N.Y. 1981) and "Protective Groups in Organic Chemistry" by J. F. W. McOmie (Plenum Press, London, 1973). Examples of R$^2$ and OR$^4$ protected hydroxy groups include phenoxyacetoxy, silyloxyacetoxy, (e.g. trimethylsilyloxyacetoxy and t-butyldimethylsilyloxyacetoxy), and silyloxy such as trimethylsilyloxy and t-butyldimethylsilyloxy. Compounds of the invention containing such groups will primarily be of use as intermediates. Other groups, such as acetoxy, may serve as protected hydroxyl groups, but may also be present in final active compounds.

Compounds of the invention have antibiotic activity e.g. antihelminthic activity, for example against nematodes, and in particular, anti-endoparasitic and anti-ectoparasitic acitivity.

The compounds of the invention are therefore of use in treating animals and humans with endoparasitic and/or ectoparasitic infections.

Ectoparasites and endoparasites infect humans and a variety of animals and are particularly prevalent in farm animals such as pigs, sheep, cattle, goats and poultry (e.g. chickens and turkeys), horses, rabbits, game-birds, caged birds, and domestic animals such as dogs, cats, guinea pigs, gerbils and hamsters. Parasitic infection of livestock, leading to anaemia, malnutrition and weight loss is a major cause of economic loss throughout the world.

Examples of genera of endoparasites infecting such animals and/or humans are Ancylostoma, Ascaridia, Ascaris, Aspicularis, Brugia, Bunostomum, Capillaria, Chabertia, Cooperia, Dictyocaulus, Dirofilaria, Dracunculus, Enterobius, Haemonchus, Heterakis, Loa, Necator, Nematodirus, Nematospiroides (Heligomoroides), Nippostrongylus, Oesophagostomum, Onchocerca, Ostertagia, Oxyuris, Parascaris, Strongylus, Strongyloides, Syphacia, Toxascaris, Toxocara, Trichonema, Trichostrongylus, Trichinella, Trichuris, Triodontophorus, Uncinaria and Wuchereria.

Examples of ectoparasites infecting animals and/or humans are arthropod ectoparasites such as biting insects, blowfly, fleas, lice, mites, sucking insects, ticks and other dipterous pests.

Examples of genera of such ectoparasites infecting animals and/or humans are Ambylomma, Boophilus, Chorioptes, Culliphore, Demodex, Damalinia, Dermatobia, Gastrophilus, Haematobia, Haematopinus, Haemophysalis, Hyaloma, Hypoderma, Ixodes, Linognathus, Lucilia, Melophagus, Oestrus, Otobius, Otodectes, Psorergates, Psoroptes, Rhipicephalus, Sarcoptes, Stomoxys and Tabanus.

The compounds according to the invention have been found to be effective both in vitro and in vivo against a range of endoparasites and ectoparasites. The antibiotic activity of compounds of the invention may, for example, be demonstrated by their activity against free living nematodes e.g. *Caenorhabiditis elegans*. In particular, we have found that compounds of the invention are active in vivo against parasitic nematodes such as *Nematospiroides dubius* and *Nippostrongylus braziliensis*.

Compounds of the invention are also of use as antifungals, for example, against strains of Candida sp. such as *Candida albicans* and *Candida glabrate* and against yeast such as *Saccharomyces carlsbergensis*.

Compounds of the invention are also of use in combating insect, acarine and nematode pests in agriculture, horticulture, forestry, public health and stored products. Pests of soil and plant crops, including cereals (e.g. wheat, barley, maize and rice), cotton, tobacco, vegetables (e.g. soya), fruit (e.g. apples, vines and citrus) as well as root crops (e.g. sugarbeet, potatoes) may usefully be treated. Particular examples of such pests are fruit mites and aphids such as *Aphis fabae, Aulacorthum circumflexum, Myzus persicae, Nephotettix cincticeps, Nilparvata lugens, Panonychus ulmi, Phorodon humuli, Phyllocoptruta oleivora, Tetranychus urticae* and members of the genera Trialeuroides; nematodes such as members of the genera Aphelencoides, Globodera, Heterodera, Meloidogyne and Panagrellus; lepidoptera such as Heliothis, Plutella and Spodoptera; grain weevils such as *Anthonomus grandis* and *Sitophilus granarius*; flour beetles such as *Tribolium castaneum*; flies such as *Musca domestica*; fire ants; leaf miners; *Pear psylla; Thrips tabaci;* coakroaches such as *Blatella germanica* and *Periplaneta americana* and mosquitoes such as *Aedes aegypti.*

According to the invention we therefore provide compounds of formula (I) as defined above, which may be used as antibiotics. In particular, they may be used in the treatment of animals and humans with endoparasitic, ectoparasitic and/or fungal infections and in agriculture, horticulture, or forestry as pesticides to combat insect, acarine and nematode pests. They may also be used generally as pesticides to combat or control pests in other circumstances, e.g. in stores, buildings or other public places or location of the pests. In general the compounds may be applied either to the host (animal or human or plants or vegetation) or a locus thereof or to the pests themselves.

Compounds of the invention may be formulated for administration in any convenient way for use in veterinary or human medicine and the invention therefore includes within its scope pharmaceutical compositions comprising a compound in accordance with the invention adapted for use in veterinary or human medicine. Such compositions may be presented for use in conventional manner with the aid of one or more suitable carriers or excipients. The compositions of the invention include those in a form especially formulated for parenteral (including intramammary administration), oral, rectal, topical, implant, ophthalmic, nasal or genito-urinary use.

The compounds according to the invention may be formulated for use in verterinary or human medicine by injection and may be presented in unit dose form, in ampoules, or other unit-dose containers, or in multidose containers, if necessary with an added preservative. The compositions for injection may be in the form of suspensions, solutions, or emulsions, in oily or aqueous vehicles, and may contain formulatory agents such as suspending, stabilising, solubilising and/or dispersing agents. Alternatively the active ingredient may be in sterile powder form for reconstitution with a suitable vehicle, e.g. sterile, pyrogen-free water, before use. Oily vehicles include polyhydric alcohols and their esters such as glycerol esters, fatty acids, vegetable oils such as arachis oil or cottonseed oil, mineral oils such as liquid paraffin, and ethyl oleate and other similar compounds. Other vehicles such as propylene glycol may also be used.

Compositions for veterinary medicine may also be formulated as intramammary preparations in either long acting or quick-release bases and may be sterile solutions or suspensions in aqueous or oily vehicles optionally containing a thickening or suspending agent such as soft or hard paraffins, beeswax, 12-hydroxy stearin, hydrogenated caster oil, aluminium stearates, or glyceryl monostearate. Conventional non-ionic, cationic or anionic surface active agents may be used alone or in combination in the composition.

The compounds of the invention may also be presented for veterinary or human use in a form suitable for oral administration, for example in the form of solutions, syrups or suspensions, or a dry powder for constitution with water or other suitable vehicle before use, optionally with flavouring and colouring agents. Solid compositions such as tablets, capsules, lozenges, pills, boluses, powder, pastes, granules, bullets or premix preparations may also be used. Solid and liquid compositions for oral use may be prepared according to methods well known in the art. Such compositions may also contain one or more pharmaceutically acceptable carriers and excipients which may be in solid or liquid form. Examples of suitable pharmaceutically acceptable carriers for use in solid dosage forms include binding agents (e.g. pregelatinised maize starch, polyvinylpyrrolidone or hydroxypropyl methylcelluslose); fillers (e.g. lactose, micro-crystalline cellulose or calcium phosphate); lubricants (e.g. magnesium stearate, talc or silica); disintegrants (e.g. potato starch or sodium starch glycollate); or wetting agents (e.g. sodium lauryl sulphate). Tablets may be coated by methods well known in the art.

Examples of suitable pharmaceutically acceptable additives for use in liquid dosage forms include suspending agents (e.g. sorbitol syrup, methyl cellulose or hydrogenated edible fats); emulsifying agents (e.g. lecithin or acacia); non-aqueous vehicles (e.g. almond oil, oily esters or ethyl alcohol); and preservatives (e.g. methyl or propyl p-hydroxybenzoates or sorbic acid); stabilising and solubilising agents may also be included.

Pastes for oral administration may be formulated according to methods well known in the art. Examples of suitable pharmaceutically acceptable additives for use in paste formulations include suspending or gelling agents e.g. aluminium distearate or hydrogenated castor oil; dispersing agents e.g. polysorbates, non-aqueous vehicles e.g. arachis oil or oily esters; stabilising and solubilising agents. The compounds of the invention may also be administered in veterinary medicine by incorporation thereof into animals daily solid or liquid dietary intake, e.g. as part of the daily animal feed or drinking water.

The compounds of the invention may also be administered orally in veterinary medicine in the form of a liquid drench such as a solution, suspension or dispersion of the active ingredient together with a pharmaceutically acceptable carrier or excipient.

The compounds of the invention may also, for examle, be formulated as suppositories e.g. containing conventional suppository bases for use in veterinary or human medicine or as pessaries e.g. containing conventional pessary bases.

Compounds according to the invention may be formulated for topical administration, for use in veterinary and human medicine, as ointments, creams, lotions, shampoos, powders, pessaries, sprays, dips, aerosols, drops (e.g. eye or nose drops) or pour-ons. Ointments and creams may, for example, be formulated with an aqueous or oily base with the addition of suitable thickening and/or gelling agents. Ointments for administration to the eye may be manufactured in a sterile manner using sterilised components. Pour-ons may, for example, be formulated for veterinary use in oils containing organic solvents, optionally with formulatory agents e.g. stabilising and solubilising agents.

Lotions may be formulated with an aqueous or oily base and will in general also contain one or more emulsifying agents, stabilising agents, dispersing agents, suspending agents, thickening agents, or colouring agents.

Powders may be formed with the acid of any suitable powder base. Drops may be formulated with an aqueous or non aqueous base also comprising one or more dispersing agents, stabilising agents, solubilising agents or suspending agents. They may also contain a preservative.

For topical administration by inhalation the compounds according to the invention may be delivered for use in veterinary or human medicine in the form of an aerosol spray presentation or an insufflator.

The compounds of the invention may be administered in combination with other pharmaceutically active ingredients.

The total daily dosages of compounds of the invention employed in both veterinary and human medicine will suitably be in the range 1–2000 μg/kg bodyweight, preferably from 50–1000 μg/kg and these may be given in divided doses, e.g. 1–4 times per day.

The compounds according to the invention may be formulated in any convenient way for horticultural or agricultural use and the invention therefore includes within its scope compositions comprising a compound according to the invention adapted for horticultural or agricultural use. Such formulations include dry or liquid types, for example dusts, including dust bases or concentrates, powders, including soluble or wettable powders, granulates, including microgranules and dispersible granules, pellets, flowables, emulsions such as dilute emulsions or emulsifiable concentrates, dips such as root dips and seed dips, seed dressings, seed pellets, oil concentrates, oil solutions, injections e.g. stem injections, sprays, smokes and mists.

Generally such formulations will include the compound in association with a suitable carrier or diluent. Such carriers may be liquid or solid and designed to aid the application of the compound either by way of dispersing it where it is to be applied or to provide a formulation which can be made by the user into a dispersible preparation. Such formulations are well known in the art and may be prepared by conventional methods such as, for example by blending and/or grinding of the active ingredient(s) together with the carrier or diluent, e.g. solid carrier, solvent or surface active agent.

Suitable solid carriers, for use in the formulations such as dusts, granulates and powders may be selected from for example natural mineral fillers, such as diatomite, talc, kaolinite, montmorillonite prophyllite or attapulgite. Highly dispersed silicic acid or highly dispersed absorbent polymers may, if desired, by included in the composition. Granulated adsorptive carriers which may be used may be porous (such as pumice, ground brick, sepiolite or bentonite) or non-porous (such as calcite or sand). Suitable pregranulated materials which may be used and which may be organic or inorganic include dolomite and ground plant residues.

Suitable solvents for use as carriers or diluents include aromatic hydrocarbons, aliphatic hydrocarbons, alcohols and glycols or ethers thereof, esters, ketones, acid amides, strongly polar solvents, optionally epoxidized vegetable oils and water.

Conventional non-ionic, cationic or anionic surface-active agents, e.g. ethoxylated alkyl phenols and alcohols, alkali metal or alkaline earth metal salts or alkyl benzene sulphonic acids, lignosulphonic acids or sulphosuccinic acids or sulphonates of polymeric phenols which have good emulsifying, dispersing and/or wetting properties may also be used either along or in combination in the compositions.

Stabilizers, anti-caking agents, anti-foaming agents, viscosity regulators, binders and adhesives, photostabilisers as well as fertilizers, feeding stimulants or other active substances may, if desired, be included in the compositions. The compounds of the invention may be formulated in admixture with other insecticides, acaricides and nematicides.

In the formulations, the concentration of active material is generally from 0.01 to 99% and more preferably between 0.01% and 40% by weight.

Commercial products are generally provided as concentrated compositions to be diluted to an appropriate concentration, for example from 0.001 to 0.0001% by weight, for use.

The compounds of the invention will be prepared by the processes discussed below. In some of these processes it may be necessary to protect the hydroxyl group at the 5- or 23- position in the starting material prior to effecting to reaction described. In such cases it may then be necessary to deprotect the same hydroxyl group once the reaction has occurred to obtain the desired compound of the invention. Conventional protection and deprotection methods may be used, for example as described in the aforementioned books by Greene and McOmie.

Thus, for example, an acyl group such as an acetyl group may be removed by basic hydrolysis e.g. using sodium or potassium hydroxide in aqueous alcohol. Acetal groups such as tetrahydropyranyl may be removed for example, using acid hydrolysis (using an acid such as acetic or trifluoroacetic acid or a dilute mineral acid). Silyl groups may be removed using fluoride ions (e.g. from a tetraalkylammonium fluoride such as tetra-n-butylammonium fluoride), hydrogen fluoride in aqueous acetonitrile or an acid such as p-toluene sulphonic acid (e.g. in methanol). Arylmethyl groups may be removed by treatment with a Lewis acid (e.g. boron trifluoride-etherate) in the presence of a thiol (e.g. ethanethiol) in a suitable solvent such as dichloromethane at e.g. room temperature.

According to one aspect of the invention we provide a process for the preparation of compounds of formula (I) in which at least one of $R^2$ and $OR^4$ is a phosphate ester group which comprises phosphorylating compounds of formula (II):

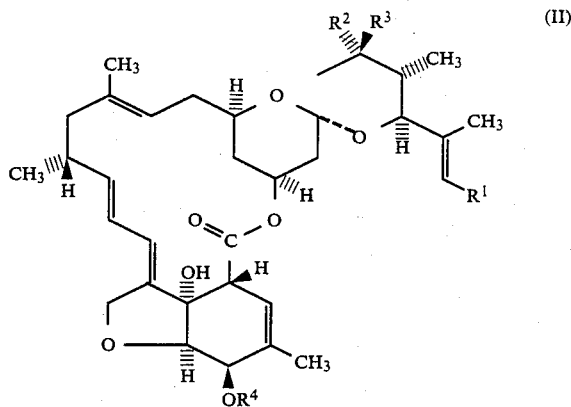

(where $R^1$ is as previously defined and at least one of $R^2$ and $OR^4$ is a hydroxyl group) with a reagent to convert a hydroxyl group into a phosphate ester group, and if desired followed by selective deprotection of a compound of formula (I) in which —$OR^4$ is a protected hydroxyl group.

The phosphorylation may be effected by conventional means, for example by reaction of a compound of formula (II) with a phosphorohalide, preferably in the presence of a base, e.g. a tertiary amine such as 4-dimethylaminopyridine, triethylamine or diisopropylethylamine or pyridine in an inert solvent such as tetrahydrofuran.

Substituted phosphate esters may conveniently be prepared by phosphorylating with a substituted phosphorohalide such as a bis(2,2,2-trichloroethyl) phosphorohalide e.g. bis(2,2,2-trichloroethyl) phosphorochloride.

Phosphate esters in which $R^2$ and/or $OR^4$ in compounds of formula (I) are $-OP(O)(OH)_2$ may be prepared by phosphorylating with phosphorous oxychloride followed by hydrolysis.

Alternatively, phosphate esters in which $R^2$ and/or $OR^4$ in compounds of formula (I) are $-OP(O)(OH)_2$ may be prepared by reduction of the corresponding compound of formula (I) in which $OR^4$ and/or $OR^5$ are $-OP(O)(OCH_2CCl_3)_2$.

The reduction may be performed using for example zinc activated by a metal such as silver. The reaction is preferably carried out in a pyridine solution at a high temperature e.g. reflux.

In a further process, a compound of formula (I) in which $R^2$ and/or $OR^4$ are $-OP(O)(OH)(OZ)$ or $-OP(O)(OZ)_2$ may be prepared from a corresponding compound of formula (I) in which $OR^2$ and/or $OR^4$ are $-OP(O)(OH)_2$ by reaction with one or two equivalents of an appropriate alkali metal hydroxide, or by contact with an ion-exchange resin, e.g. a polystyrene resin such as Dowex, containing the appropriate alkali metal counterion.

In general, the hydroxy group at the 5-position of the compounds of formula (II) is more reactive than that at the 23-position and is phosphorylated first. The extent to which phosphorylation occurs at the 23-position is therefore dependent on the amount of phosphorylating reagent used.

According to a further aspect of the invention we provide a process for the preparation of compounds of formula (I) in which at least one of $R^2$ and $OR^4$ is a group $OCONR^{10}R^{11}$ which comprises reacting compounds of formula (II): ($R^1$ is as previously defined and at least one of $R^2$ and $OR^4$ is a hydroxyl group) with a reagent serving to convert a hydroxyl group into a group $OCONR^{10}R^{11}$, and if desired followed by selective deprotection of a compound of formula (I) in which $OR^4$ is a protected hydroxyl group.

Thus, carbamoylation may be effected by conventional methods using suitable acylating (i.e. carbamoylating) agents. Suitable carbamoylating agents include isocyanates of formula $R^{12}NCO$ (wherein $R^{12}$ is a $C_{1-4}$ alkyl group). The carbamoylation reaction may desirably be effected in the presence of a solvent or solvent mixture selected from hydrocarbons (e.g. aromatic hydrocarbons such as benzene and toluene), halogenated hydrocarbons (e.g. dichloromethane), amides (e.g. formamide or dimethylformamide), esters (e.g. ethyl acetate), ethers (e.g. cyclic ethers such as tetrahydrofuran and dioxan), ketones (e.g. acetone), sulphoxides (e.g. dimethylsulphoxide) and mixtures of these solvents. The reaction may conveniently be carried out at a temperature of between $-80°$ C. and the boiling temperature of the reaction mixture, for example up to $100°$ C., preferably between $-20°$ and $+30°$ C.

The carbamoylation may be assisted by the presence of a base, e.g. a tertiary organic base such as a tri-(lower alkyl)amine (e.g. triethylamine).

Another useful carbamoylating agent is cyanic acid, which is conveniently generated in situ, for example, from an alkai metal cyanate such as sodium cyanate, the reaction being facilitated by the presence of an acid, e.g. a strong organic acid such as trifluoroacetic acid. Cyanic acid effectively corresponds to the isocyanate compounds mentioned above wherein $R^{12}$ is hydrogen and therefore converts compounds of formula (II) directly to their carbamoyloxy analogues.

Alternatively, corbamoylation may be effected by reaction of the compound of formula (II) with phosgene or carbonyldiimidazole followed by ammonia or the appropriate substituted amine, optionally in an aqueous or non-aqueous reaction medium.

In a further process according to the invention a compound of formula (I) in which at least one of $R^2$ and $OR^4$ is a group $OCONR^{10}R11$ may be prepared by reaction of a compound of formula (II) in which $R^1$ is as defined previously and one or both of $R^2$ and $OR^4$ is a group $OCO_2R^6$ with an amine $R^{10}R^{11}NH$ (where $R^{10}$ and $R^{11}$ are as defined previously). The reaction may be carried out in a suitable solvent, conveniently at a temperature of from $-50°$ to $+50°$ C., preferably $-5°$ to $+30°$ C. Suitable solvents include halogenated hydrocarbons e.g. dichloromethane, nitriles e.g. acetonitrile, amides e.g. N,N-dimethylformamide, ethers e.g. tetrahydrofuran or dioxan and alcohols e.g. ethanol or mixtures of such solvents.

According to another aspect of the invention we provide a process for the preparation of compounds of formula (I) in which $R^2$ represents a group $OR^5$ where $OR^5$ is an alkoxy group $OR^7$ in which $R^7$ is a $C_{1-6}$ alkyl group substituted by a halogen atom or a $C_{2-6}$ alkyl group interrupted by an oxygen or sulphur atom which comprises reacting compounds of formula (II) (in which $R^1$ is as previously defined, $R^2$ is a hydroxy group, $R^3$ is a hydrogen atom and $-OR^4$ is a substituted hydroxyl group) with a reagent serving to convert a hydroxyl group into a group $OR^5$ (where $R^5$ is as just defined), and if desired followed by selective deprotection of a compound of formula (I) in which $-OR^4$ is a protected hydroxyl group.

Thus, etherification may be effected by conventional methods using a reagent $R^5Y$ (where $R^5$ is as just defined and Y represents a leaving group such as a chlorine, bromine or iodine atom, or a hydrocarbylsulphonyloxy group e.g. mesyloxy or tosyloxy, or a haloalkanoyloxy group e.g. dichloroacetoxy).

The reaction may be carried out by initial formation of a magnesium alkoxide using a Grignard reagent such as a methylmagnesium halide e.g. methylmagnesium iodide or using a trialkylsilylmethylmagnesium halide e.g. trimethylsilylmethylmagnesium chloride followed by treatment with the reagent $R^5Y$.

Alternatively, the reaction may be effected in the presence of a silver salt such as silver oxide, silver perchlorate, silver carbonate or silver salicylate or mixtures thereof, and this system may be particularly appropriate when the etherification is carried out using a reagent $R^5Y$ wherein Y is a halogen atom.

Etherification may conveniently be effected in a solvent such as an ether e.g. diethyl ether.

Compounds of formula (I) wherein $R^2$ and/or $OR^4$ is a substituted hydroxyl group may be prepared from the corresponding 5 and/or 23-OH compounds using the methods described in UK Patent Specification No. 2176182A.

The compounds of formula (II) are described in UK Patent Specification No. 2176182A.

The invention is further illustrated by the following Examples in which the compounds are named by reference to the known parent 'Factors', Factors A and B. Factor A (described in UK Patent Specification No. 2166436A) is a compound of formula (II) in which $R^1$ is isopropyl, $R^2$ and $OR^4$ are hydroxyl groups and $R^3$ is a hydrogen atom. Factor B (also described in UK Patent Specification No. 2166436A) is a compound of formula (II) in which $R^1$ is methyl, $R^2$ is a hydroxyl group, $R^3$ is a hydrogen atom and $OR^4$ is a methoxy group. All temperatures are in °C.

EXAMPLE 1

5-O-(bis-2,2,2-Trichloroethyl)phosphono Factor A

A solution of Factor A (195 mg, azeotropically dried with toluene) in dry tetrahydrofuran (3 ml) was treated, under a nitrogen atmosphere, with freshly distilled dry N,N-diisopropylethylamine (0.55 ml) followed by 2,2,2-trichloroethyl phosphonochloridate (522 mg) and 4-dimethylaminopyridine (56 mg). After 3¾ h. the brown mixture was poured into ether (30 ml) then washed with water (10 ml) N hydrochloric acid (2×10 ml), saturated sodium bicarbonate (10 ml), water and brine. Evaporation of the dried organic phase give a gum (522 mg). The gum as a solution in hexane: ethyl acetate (3:1) was applied to a column of Kieselgel 60, 70–230 mesh silica (50 g) and eluted with the same solvent system to give the title compound (111 mg) $[\alpha]_D^{21} + 80°$ (c 0.5 $CHCl_3$), $\lambda_{max}^{EtOH}$ 245 nm ($\epsilon$max 29,000), $\nu$max 3500 (OH), 1710 (C=O) abd 1015 $cm^{-1}$ (P—O—C); $\delta(CDCl_3)$ includes 0.8 (3, 6 Hz; 3H), 0.96 (d, 7 Hz; 3H), 1.00 (d, 6 Hz; 3H), 1.05 (d, 7 Hz; 3H), 1.54 (s; 3H), 1.61 (2; 3H), 1.90 (s; 3H), 3.36 (m; 1H), 3.75 (d, 10 Hz; 1H), 4.13 (d, 6 Hz; 1H), 4.5–4.8 (m; 6H), 5.58 (brs; 1H)

EXAMPLE 2

— 5-O-Phosphono Factor A

A well stirred solution of 5-O-(bis-2,2,2-trichloroethyl)phosphono Factor A (100 mg) in a mixture of pyridine:water [9:1 (2 ml)] was treated with moist, freshly prepared zinc/silver reagent (150 mg wet weight) and the mixture heated to reflux for 5 min. This procedure was repeated four times until reaction was complete. The mixture was cooled and centrifuged. The supernatent was decanted, the residue washed with fresh pyridine:water [9:1 (2 ml)] and the combined liquid phases concentrated in vacuo. The residual liquid was partitioned between ethylacetate (40 ml) and N hydrochloric acid (20 ml). The aqueous phase was separated and extracted with ethyl acetate (3×10 ml). The combined orgaic extracts were washed with 2N hydrochloric acid (10 ml), water (10 ml) and finally brine (20 ml). The organic phase was dried and evaporated to leave a yellow residue which was dissolved in 80% aqueous ethanol and passed through a short column of Amberlite XAD2, 20 to 50 mesh, polymeric adsorbent beads. Appropriate fractions were combined and concentrated in vacuo. The residue was then passed through a column of Dowex 50 (H+), ion exchange resin (10 g) to afford the title compound as a light white solid (40 mg) $\nu$max (CHBr₃) 3390 to 3610 (OH), 1710 $cm^{-1}$ (C=O)$\delta$(CDCl₃) includes 0.9 (d, 6 Hz; 3H), 0.95 (d, 6 Hz; 3H), 0.98 (d, 6 Hz; 3H), 1.05 (d, 6 Hz; 3H), 1.52 (s; 3H), 1.60 (s, 3H), 1.79 (s; 3H), 3.27 (m; 1H), 3.74 (d, 10 Hz; 1H), 4.12 (d, 5 Hz; 1H), 5.44 (brs, 1H).

Passage of a solution of the title compound in water through a column of Dowex 50, ion exchange resin (Na form, 10 g) afforded the corresponding mono sodium salt which gave $\lambda_{max}^{EtOH}$ 245.5 nm ($\epsilon$max 15,000) and m/z=714 (M+).

EXAMPLE 3

5-Acetoxy,23-0-Phosphono Factor A

To a cold (0°–5°) solution of 5-acetoxy Factor A (Example 7 in UK-2176182A (604 mg) (azeotropically dried with toluene) in dry pyridine (0.24 ml) and dry tetrahydrofuran (4 ml) under nitrogen, was added, in one portion phosphorous oxychloride (0.24 ml). After 10 min at 0° to 5° and 24 h at 21°, the resulting mixture was partitioned between ethyl acetate (40 ml) and water (20 ml). The aqueous phase was separated, and extracted with ethyl acetate (2×20 ml), water (20 ml) and brine and the organic phase was then concentrated in vacuo to ca 50 ml. The concentrate was extracted thoroughly with saturated aqueous sodium bicarbondate and the combined aqueous solution acidified under ethyl acetate (600 ml) with 2N hydrochloric acid to pH2. The aqueous phase was then re-extracted with ethyl acetate (2×200 ml) and the combined organic extract then washed with water (100 ml) and brine. Evaporation of the dried organic phase afforded a pale brown foam (171 mg) which was purified by preparative reverse phase HPLC to give, after freeze-drying the aqueous eluate, the title compound as a light fluffywhite solid (100 mg) $[\alpha]_D^{21} + 128°$ (c 0.34, $CHCl_3$), $\lambda_{max}^{EtOH}$ 243.8 nm ($\epsilon_{max}$ 27,200); $\nu_{max}$ (CHBr₃) 2500 to 3700 (OH), 1739 and 1720 $cm^{-1}$ (ester); $\delta(CDCl_3 + 1$ drop $CH_3CO_2H$) includes 0.77 (d,6 Hz; 3H), 0.95 (d,6 Hz;3H), 1.00 (d,6 Hz;3H), 1.05 (d,6 Hz;3H), 1.52 (s;3H) 1.60 (s;3H), 1.74 (s; 3H), 2.16 (s;3H), 3.33 (m,1H), 3.93 (d,10 Hz;1H), 4.40 (brs;1H) and 5.5 to 5.6 (m;2H).

Passage of a solution of the title compound in water through a Dowex 50 (Na form) ion exchange resin, afforded the corresponding mono sodium salt which gave $\lambda_{max}^{EtOH}$ 245.5 nm ($\epsilon_{max}$ 16,300) and m/z=779 (M=Na)+.

EXAMPLE 4

23-0-Phosphono Factor A

A solution of 5-Acetoxy, 23-0-phosphono Factor A (34 mg) in methanol (1.0 ml) was cooled to 0°–5° and treated with aqueous sodium hydroxide (1M, 0.14 ml). After 2 h at 0° to 5°, the solution was partitioned between ether (15 ml) and 2N hydrochloric acid (10 ml). The aqueous phase was separated and extracted with ether (10 ml). Evaporation of the dried organic phase afforded a yellow solid which as a solution in 10% acetonitrile was freeze-dried to give the title compound as a white fluffy solid (18 mg) $[\alpha]_D^{21} + 72°$ (c 0.23, $CHCl_3)\nu_{max}$ (CHBr) 3500 (OH) and 1708 $cm^{-1}$ (ester), $\delta(CDCl_3 + 1$ drop $CH_3CO_2H$) includes 0.75 (d,6 Hz;3H), 3.93 (d,10 Hz;1H) and 4.3 to 4.4 (m;2H).

EXAMPLE 5

5-Acetoxy-23-(3-chloropropyloxy) Factor A 3-chloro-1-iodopropane (1 ml) was added to a solution of 5-acetoxy Factor A (0.4 g) in dry ether (50 ml), followed by silver carbonate (1.20 g), then silver perchlorate (0.87 g). The mixture was stirred at room temperature for 20 h. then diluted with ethyl acetate, filtered, and the filtrate treated with collidine (2 ml) and methanol (2 ml). After 2 h the mixture was washed successively with 0.5N hydrochloric acid and water. The dried organic phase was evaporated and the oil was purified by chromatography over Merk Keiselgel 60 230–400 mesh (100 ml). Elution of the column with hexane: ethyl acetate (4:1) afforded the title compound as a colourless foam (0.327 g) $[\alpha]^{21}_D + 150°$ (c 1.65, CHCl$_3$) $\lambda_{max}$ (EtOH) 244 nm ($\epsilon_{max}$ 29,250), $\nu_{max}$ (CHBr$_3$) 3540, 3470 (OH), 1731 (acetate), 1708 (C=O), 999 (C—O), $\delta$(CDCl$_3$) include 5.5–5.6 (m;2H), 3.70 (t;2H), 3.6–3.8 (hidden m;1H), 3.46 (m;1H) 3.2–3.4 (m;2H) 2.17(S;3H).

Example 6 was prepared in a similar manner from 5-acetoxy Factor A and the appropriate alkylating agent.

EXAMPLE 6

5-Acetoxy-23[(2-ethoxy)ethoxy] Factor A $[\alpha]^{21}_D + 158°$ (c 1.22, CHCl$_3$) $\lambda_{max}$ (EtOH) 244 nm ($\epsilon_{max}$ 31,500) . $\nu_{max}$ (CHBr$_3$) 3530, 3470 (OH), 1732 (acetate), 1708 (C=O), 997 (C—O), (C=O), 997 (C—O), $\delta$(CDCl$_3$) include 5.5–5.6 (m;2H), 3.74 (m;1H), 3.5–3.7 (m;6H), 3.41 (m;1H), 2.16 (s;34) was prepared from 2-bromoethyl ethyl ether

EXAMPLE 7

5-Acetoxy-23-methoxymethoxy Factor A

A 3M solution of methylmagnesium iodide in ether (0.45 ml) was added to a stirred solution of 5-acetoxy Factor A (733 mg) in dry hexamethylphosphortriamide (15 ml) under nitrogen, with immediate effervescence. After 20 min a solution of bromomethyl methyl ether (171 mg) in ether (0.6 ml) was added. After 1 h further ethereal 3M methylmagnesium iodide solution (0.3 ml) was added, followed by a solution of bromomethyl methyl ether (86 mg) in ether (0.3 ml). The mixture was stirred at room temperature for 20 h, diluted with ether (100 ml) and washed with water. The dried organic phase was evaporated and the resultant gum was purified by chromatography over Merck Keiselgel 60 230–400 mesh (150 ml). Elution of the column with hexane: ethyl acetate (2:1) afforded the title compound as a colourless foam (499 mg) $[\alpha]^{23}_D + 175°$ (c 1.40, CHCl$_3$) $\lambda_{max}$ (EtOH) 244 nm ($\epsilon_{max}$ 27,600) $\nu_{max}$ (CHBr$_3$) 3540, 3470 (OH), 1734 (acetate) 1712 (C=O), 995 (C—O), $\delta$(CDCl$_3$) include 5.5–5.6 (m;2H), 4.80 (d7;1H), 3.76 (m;1H), 3.40 (s;3H), 2.16 (s;3H).

Example 8 was prepared in a similar manner from 5-acetoxy Factor A and the appropriate alkylating agent

EXAMPLE 8

5-Acetoxy-23-methylthiomethoxy Factor A $[\alpha]^{21}_D + 189°$ (c 1.19 CHCl$_3$), $\lambda_{max}$ (EtOH) 244 nm ($\epsilon_{max}$ 28,950), $\nu_{max}$ (CHBr$_3$) 3470 (OH), 1734 (acetate), 1712 (C=O), 994 (C—O), $\delta$(CDCl$_3$) include 5.5–5.6 (m;2H), 4.5–4.8 (m;4H), 2.16 (s;3H), 2.14 (s;3H) was prepared from chloromethyl methyl sulphide.

EXAMPLE 9

5-Acetoxy-23-(3-iodopropyloxy) Factor A

A solution containing 5-acetoxy-23-(3-chloropropyloxy)-Factor A (140 mg) and sodium iodide (330 mg) in acetone (15 ml) was heated under reflux for 5 days. The cooled solution was diluted with ether (50 ml), washed with water, and the dried organic phase was evaporated to afford a gum which was purified by chromatography over Merk Keiselgel 60 230–400 mesh (60 ml). Elution of the column with hexane:ethyl acetate (3:1) afforded the title compound as a colourless foam (136 mg) $[\alpha]^{21}_D + 140°$ (c 103, CHCl$_3$, $\lambda_{max}$ (EtOH) 244 nm ($\epsilon_{max}$ 31,300) $\nu_{max}$ (CHBr$_3$) 3530, 3460 (OH), 1732 (acetate); 1710 (C=O), 996 (C—O), $\delta$(CDCl$_3$) includes 5.5–5.6 (m;2H), 3.5–3.7 (m;2H), 3.45 (m;1H), 3.36 (t7;2H, 3.26 (m;1H), 2.16 (s;3H).

EXAMPLE 10

23-Methoxymethoxy Factor A

A solution of 5-acetoxy-23-methoxymethoxy Factor A (471 mg) in methanol (30 ml) was cooled in an ice bath, 1N aqueous sodium hydroxide (1.5 ml) was added and the solution was stirred in an ice bath for 1.25 h. The solution was diluted with ether (80 ml), then washed successively with 0.5N hydrochloric acid, then water. The dried organic phase was evaporated and the resultant gum was purified by chromatography over Merk Keiselgel 60 230–400 mesh (140 ml). Elution of the column with hexane:ethyl acetate (2:1) afforded the title compound as a colourless foam (260 mg) $[\alpha]^{23}_D + 175°$, (c 1.40, CHCl$_3$), $\lambda_{max}$ (EtOH) 244 nm ($\epsilon_{max}$ 26,900), $\nu_{max}$ (CHBr$_3$) 3560, 3480 (OH), 1708 (C=O), 998 (C—O), $\delta$(CDCl$_3$) include 4.80 (d7;1H), 4.56 (d7;1H), 4.29 (t7;1H), 3.76 (m;1H) 3.40 (s;3H).

Examples 11–14 were prepared in a similar manner

EXAMPLE 11

23-Methylthiomethoxy Factor A $[\alpha]^{21}_D + 186°$ (c 1.35 CHCl$_3$), $\lambda_{max}$ (EtOH) 244 nm ($\epsilon_{max}$ 28,800), $\nu_{max}$ (CHBr$_3$) 3550, 3470 (EtOH), 1707 (C=O), 993 (C—O), $\delta$(CDCl$_3$) include 4.6–4.8 (m;4H), 4.29 (t7;1H), 3.90 (m;1H), 2.15 (s;3H) was prepared from 5-acetoxy-23-methylthiomethoxy Factor A.

EXAMPLE 12

23-[(2-Ethoxy)ethoxy] Factor A $[\alpha]^{21}_D + 146°$ (c 1.28, CHCL$_3$), $\lambda_{max}$ (EToH) 244 mm ($\epsilon_{max}$ 27,700); $\nu_{max}$ (CHBr$_3$) 3550, 3480 (OH), 1706 (C=O), 999 (C—O), $\delta$(CDCl$_3$) include 4.30 (t7;1H), 3.74 (m;1H), 3.5–3.7 (m;6H), 3.41 (m;1H), 1.20 (t7;3H) was prepared from 5-acetoxy-23-[(2-ethoxy)ethoxy] Factor A.

EXAMPLE 13

23-(3-Chloropropyloxy) Factor A $[\alpha]^{21}_D + 150°$ (c 1.46, CHCl$_3$), $\lambda_{max}$ (EtOH) 244 nm ($\epsilon_{max}$ 27,200), $\nu_{max}$ (CHBr$_3$) 3550, 3470 (OH), 1706 (C=O), 999 (C—O), $\delta$(CDCl$_3$) include 4.29 (br.s;1H), 3.70 (t;7.2H), 3.6–3.8 (hidden m;1H) 3.45 (m;1H) 3.33 (m;1H) was prepared from 5-acetoxy-23-(3-chloropropyloxy) Factor A.

EXAMPLE 14

23-(3-Iodopropyloxy) Factor A $[\alpha]^{21}_D + 137°$ (c 1.48, CHCl$_3$), $\lambda_{max}$ (EtOH) 244 nm ($\epsilon_{max}$ 29,200), $\nu_{max}$ (CHBr$_3$) 3555, 3480 (OH) 1707 (C=O), 995 (C—O), $\delta$(CDCl$_3$) include 4.29 (t7;1H), 3.5–3.7 (m;2H), 3.45 (m;1H), 3.36 (t7;2H), 3.2–3.3 (m;2H) was prepared from 5-acetoxy-23-(3-iodopropyloxy) Factor A. $[\alpha]^{20}_D + 142°$ (c 0.92, CHCl$_3$); $\lambda_{max}$ (EtOH) 245 nm ($\epsilon$29,200); $\nu_{max}$ (CHBr$_3$) 3560 and 3500 (OH), 1745 carbonate, and 1710 cm$^{-1}$ (ester), $\delta$(CDCl$_3$) include 5.40 (s, 1H), 4.80 and 4.70 (ABq, J14 Hz, 2H), 4.28 (m, 1H) and 0.79 (d, J7 Hz, 3H).

EXAMPLE 15

Factor A, 23-N-methylcarbamate

Factor A, 23-(2,2,2-trichloroethyl)carbonate (Example 88 in UK-2176182A) (150 mg) was dissolved in ethanol (5 ml) and 33% methylamine in ethanol (2 ml) was added. The resulting solution was stirred for 2 hours at 20°, and then poured into a mixture of ethyl acetate and 2N-hydrochloric acid (50 ml of each). The organic phase was washed with brine (25 ml), and dried (magnesium sulphate), and evaporated to dryness. The residue was purified by chromatography over Kieselgel 60 (20 g). Elution of the column with light petroleum-:ethyl acetate (1:1) gave the title compound (83 mg) as a colourless foam, $[\alpha]_D^{20} +192°$ (c 0.7, CHCl$_3$) $\lambda_{max}$ (EtOH) 245.5 nm ($\epsilon$27,800), $\nu_{max}$ (CHBr$_3$) 3560 and 3465 (OH and NH), 1710 (ester), and 1710 and 1515 cm$^{-1}$ (carbamate), $\delta$(CDCl$_3$) include 4.9 to 5.1 (m, 2H), 4.28 (t, J7 Hz, 1H), 4.54 (m, 1H), 3.86 (d, J10 Hz, 1H), 2.80 (m, 3H) and 0.71 (d, J7 Hz, 3H).

EXAMPLE 16

Factor A, 23-carbamate

A solution of Factor A, 23-(2,2,2-trichloroethyl)carbonate (246 mg) in a mixture of dioxan (10 ml) and ammonia solution (SG 0.88) (2 ml) was stirred at 20° for 16 hours, and then poured into a mixture of ethyl acetate (100 ml) and 2N-hydrochloric acid (50 ml). The organic phase was washed with brine (25 ml), and dried (magnesium sulphate), and evaporated to dryness. The residue was purified by chromatography over Kieselgel 60 (25 g). Elution of the column with light petroleum-:ethyl acetate (1:1) gave the title compound (60 mg) as a colourless foam, $[\alpha]_D^{20} +155°$ (c 0.64, CHCl$_3$), $\lambda_{max}$ (EtOH) 245.5 nm ($\epsilon$28,400), $\nu_{max}$ (CHBr$_3$) 3545 and 3430 (OH and NH), 1715 (ester) and 1715 and 1572 cm$^{-1}$ (carbamate)$\delta$(CDCl$_3$) include 4.86 (m, 1H), 4.59 (s, 2H), 4.29 (t, J7 Hz, 1H), 3.87 (d, J10 Hz, 1H) and 0.73 (d, J7 Hz, 3H).

EXAMPLE 17

Factor B, 23-N-Methylcarbamate

Factor B (300 mg), 2,2,2-trichloroethylcarbonyl chloride (1.5 ml of 1M solution in dichloromethane), and dry pyridine (0.5 ml) were stirred together for 2 h at 23° in dry dichloromethane (10 ml). The mixture was poured into ethyl acetate and the organic solution worked up for neutral material, a pale yellow gum (577 mg). The crude product in dichloromethane was introduced on to a column of Merck Kieselgel 60, 230–400 mesh silica (50 g) made up in the same solvent. Elution with dichloromethane and then dichloromethane:ether (19:1) provided a solid (250 mg) which in ethanol solution (5 ml) was treated with a 33% ethanolic solution of methylamine. After 3½ hr at room temperature the mixture was poured into ethyl acetate and the organic phase washed with 2N-hydrochloric acid and brine. Evaporation of the dried ethyl acetate layer gave a gum (200 mg) which was purified by chromatography over silica (50 g) using dichloromethane:ether (9:1) and dichloromethane:ether (4:1) as the eluting phases. The title compound was obtained as an amorphous solid (60 mg) from ether/n-pentane, $[\alpha]_D^{23} +161°$ (c 0.30, CHCl$_3$); $\lambda_{max}^{EtOH}$ 239 (27,000) and 245 nm ($\epsilon_{max}$28,900), $\nu_{max}$ (CHBr$_3$) 3460 (NH and OH), 1705 (ester) and 1705 and 1513 cm$^{-1}$ (carbamate) $\delta$(CDCl$_3$) include 2.79 (d,5 Hz,3H), (s,3.51, 3H) 4.55 (q, 5 Hz, 1H) and 4.9–5.1 (m, 2H), m/z=655 (M+).

EXAMPLE 18

Factor A, 5-N-methylcarbamate

Factor A (306 mg), excess methyl iscyanate (116 mg) and two drops of dimethylamine were heated together in dry N,N-dimethylformamide (0.6 ml) in a sealed vessel at 80° for 7 h. The mixture was cooled, diluted with ether and the organic phase then washed successively with saturated aqueous sodium bicarbonate, 2N hydrochloric acid and brine. Evaporation of the dried ethanol layer gave material (356 mg) which was purified by preparative h.p.l.c. Elution with 65% acetonitrile in water afforded a foam which was dissolved in a small volume of ether. Addition of n-pentane precipitated the title compound as a white amorphous solid (100 mg), $[\alpha]_D^{23} +139°$ (c 0.36, CHCl$_3$), $\lambda_{max}$ (EtOH) 239 (28,600) and 245 nm (E$_{max}$ 31,700), $\nu_{max}$ (CHBr$_3$) 3800 (OH), 3450 (NH), and 1710 cm$^{-1}$ (ester and carbamate), $\delta$(CDCl$_3$) include 5.51 (d, 6H$_z$, 1H), 4.79 (q, 5H$_z$, 1H) and 2.82 (d, 5H$_z$, 3H).

The following are examples of formulations according to the invention. The term 'Active Ingredient' as used hereinafter means a compound of the invention.

Multidose parenteral injection

|                      | % w/v | Range         |
|----------------------|-------|---------------|
| Active Ingredient    | 4.0   | 0.1–7.5% w/v  |
| Benzyl alcohol       | 2.0   |               |
| Glyceryl triacetate  | 30.0  |               |
| Propylene glycol to  | 100.0 |               |

Dissolve the active ingredient in the benzyl alcohol and glyceryl triacetate. Add propylene glycol and make up to volume. Sterilise the product by conventional pharmaceutical methods, for example sterile filtration or by heating in an autoclave and package aseptically.

Aerosol spray

|                        | % w/w | Range           |
|------------------------|-------|-----------------|
| Active Ingredient      | 0.1   | 0.01–2.0% w/w   |
| Trichloroethane        | 29.9  |                 |
| Trichlorofluoromethane | 35.0  |                 |
| Dichlorodifluoromethane| 35.0  |                 |

Mix the Active Ingredient with trichloroethane and fill into the aerosol container. Purge the headspace with the gaseous propellant and crimp and valve into position. Fill the required weight of liquid propellant under pressure through the valve. Fit with actuators and dustcaps.

Tablet

Method of manufacture - wet granulation

|                           | mg                               |
|---------------------------|----------------------------------|
| Active Ingredient         | 250.0                            |
| Magnesium stearate        | 4.5                              |
| Maize starch              | 22.5                             |
| Sodium starch glycolate   | 9.0                              |
| Sodium lauryl sulphate    | 4.5                              |
| Microcrystalline cellulose| to tablet core weight of 450 mg  |

Add sufficient quantity of a 10% starch paste to the active ingredient to produce a suitable wet mass for granulation. Prepare the granules and dry using a tray or fluid-bed drier. Sift through a seive, add the remaining ingredients and compress into tablets.

If required, film coat the tablet cores using hydroxypropylmethyl cellulose or other similar film-forming material using either an aqueous or non-aqueous solvent system. A plasticizer and suitable colour may be included in the film-coating solution.

Veterinary tablet for small/domestic animal use

Method of manufacture - dry granulation

|  | mg |
|---|---|
| Active Ingredient | 50.0 |
| Magnesium stearate | 7.5 |
| Microcrystalline cellulose to tablet core weight of | 75.0 |

Blend the active ingredient with the magnesium stearate and microcrystallise cellulose. Compact the blend into slugs. Break down the slugs by passing through a rotary granulator to produce free-flowing granules. Compress into tablets.

The tablet core can then be film-coated, if desired, as described above.

Veterinary intrammary injection

|  |  | mg/dose | Range |
|---|---|---|---|
| Active Ingredient |  | 150 mg | 0.05–1.0 g |
| Polysorbate 60 | 3.0% w/w | to 3 g | to 3 or 15 g |
| White Beeswax | 6.0% w/w |  |  |
| Arachis oil | 91.0% w/w |  |  |

Heat the arachis oil, white beeswax and polysorbate 60° to 160° C. with stirring. Maintain at 160° C. for two hours and then cool to room temperature with stirring. Aseptically add the active ingredient to the vehicle and disperse using a high speed mixer. Refine by passing through a colloid mill. Aseptically fill the product into sterile plastic syringes.

Veterinary oral drench

|  | % w/v | Range |
|---|---|---|
| Active Ingredient | 0.35 | 0.01–2% w/v |
| Polysorbate 85 | 5.0 |  |
| Benzyl alcohol | 3.0 |  |
| Propylene glycol | 30.0 |  |
| Phosphate buffer | as pH 6.0–6.5 |  |
| Water | to 100.0 |  |

Dissolve the active ingredient in the Polysorbate 85, benzyl alcohol and the propylene glycol. Add a proportion of the water and adjust the pH to 6.0–6.5 with phosphate buffer, if necessary. Make up to final volume with the water. Fill the product into the drench container.

Veterinary oral paste

|  | % w/w | Range |
|---|---|---|
| Active Ingredient | 7.5 | 1–30% w/w |
| Saccharin | 25.0 |  |
| Polysorbate 85 | 3.0 |  |

-continued

|  | % w/w | Range |
|---|---|---|
| Aluminium distearate | 5.0 |  |
| Fractionated coconut oil | to 100.0 |  |

Disperse the aluminium distearate in the fractionated coconut oil and polysorbate 85 by heating. Cool to room temperature and disperse the saccharin in the oily vehicle. Dispense the active ingredient in the base. Fill into plastic syringes.

Granules for verterinary in-feed administration

|  | % w/w | Range |
|---|---|---|
| Active Ingredient | 2.5 | 0.05–5% w/w |
| Calcium sulphate, hemi-hydrate | to 100.0 |  |

Blend the Active Ingredient with the calcium sulphate. Prepare the granules using a wet granulation process. Dry using a tray or fluid-bed drier. Fill into the appropriate container.

Emulsifiable Concentrate

| Emulsifiable Concentrate |  |
|---|---|
| Active ingredient | 50 g |
| Anionic emulsifier (e.g. Phenyl sulphonate CALX) | 40 g |
| Non-ionic emulsifier (e.g. Syperonic NP13) | 60 g |

Aromatic solvent (e.g. Solvesso 100) to 1 litre. Mix all ingredients, stir until dissolved.

Granules

| (a) | Active ingredient | 50 g |
|---|---|---|
|  | Wood resin | 40 g |
|  | Gypsum granules (20–60 mesh) to (e.g. Agsorb 100A) | 1 kg |
| (b) | Active ingredient | 50 g |
|  | Syperonic NP13 | 40 g |
|  | Gypsum granules (20–60 mesh) to | 1 kg. |

Dissolve all ingredients in a volatile solvent e.g. methylene chloride, add to granules tumbling in mixer. Dry to remove solvent.

We claim:

1. A compound of formula (I)

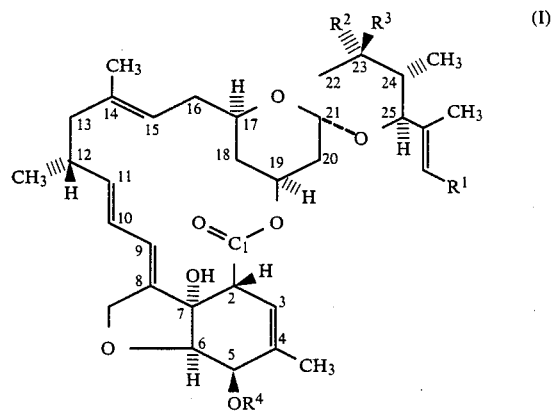

wherein
- $R^1$ is a methyl, ethyl or isopropyl group;
- $R^2$ is a hydrogen atom or a group $OR^5$ as defined below and $R^3$ is a hydrogen atom, or $R^2$ and $R^3$ together with the carbon atom to which they are attached represent a $>C=O$ group;
- $CR^5$ is a hydroxyl group; an alkoxy group $OR^7$ in which $R^7$ is a $C_{1-6}$ alkyl group substituted by a halogen atom or a $C_{2-6}$ alkyl group interrupted by an oxygen or sulphur atom; a phosphate ester group of the formula $-OP(O)(OH)_2$, $-OP(O)(OH)(OZ)$, $-OP(O)(OZ)_2$, or $-OP(O)(OCH_2CCl_3)_2$ where Z represents an alkali metal; or a group $OCONR^{10}R^{11}$ where $R^{10}$ and $R^{11}$ independently represent a hydrogen atom or a $C_{1-4}$ alkyl group;
- $OR^4$ is a hydroxyl or methoxy group, a group $-OCOR^6$ where $R^6$ is a $C_{1-4}$ alkyl group; or a phosphate ester group or a group $OCONR^{10}R^{11}$ as defined for $OR^5$;

with the proviso that either $R^2$ is a group $OR^7$ as defined above or at least one of $R^2$ and $OR^4$ is a phosphate ester group or $OCONR^{10}R^{11}$ as defined above.

2. A compound according to claim 1 in which $R^1$ is an isopropyl group.

3. A compound according to claim 1 in which $OR^4$ is an acetoxy group.

4. A compound according to claim 1 in which $OR^4$ is a hydroxy group.

5. A compound according to claim 1 in which $R^1$ is an isopropyl group, $R^3$ is a hydrogen atom, $OR^4$ is a hydroxy or acetoxy group, and $R^2$ is a methoxymethoxy, methylthiomethoxy, ethoxyethoxy, 3-halopropoxy or $-OCONR^{10}R^{11}$ group (where $R^{10}$ and $R^{11}$ independently represent a hydrogen atom or a methyl group).

6. A compound according to claim 1 in which $R^1$ is an isopropyl group, $R^2$ is a hydroxy group, $R^3$ is a hydrogen atom and $OR^4$ is $OP(O)(OH)_2$, $OP(O)(OH)(ONa)$ or $OP(O)(ONa)_2$.

7. A compound according to claim 1 in which:
- $R^1$ is an isopropyl group, $R^2$ is a methoxymethoxy group, $R^3$ is a hydrogen atom and $OR^4$ is a hydroxy group;
- $R^1$ is an isopropyl group, $R^2$ is a methylthiomethoxy group, $R^3$ is a hydrogen atom and $OR^4$ is a hydroxy group;
- $R^1$ is an isopropyl group, $R^2$ is a 3-chloropropoxy group, $R^3$ is a hydrogen atom and $OR^4$ is a hydroxy group; or
- $R^1$ is an isopropyl group, $R^2$ is an N-methylaminocarbonyloxy group, $R^3$ is a hydrogen atom and $OR^4$ is a hydroxy group.

8. A composition used in human medicine containing an effective amount of at least one compound according to claim 1 together with at least one carrier, excipient or a mixture thereof.

9. A composition for use in veterinary medicine containing an effective amount of at least one compound according to claim 1 together with at least one carrier, excipient or a mixture thereof.

10. A pest control composition containing an effective amount of at least one compound according to claim 1 together with at least one carrier, excipient or a mixture thereof.

11. A method for combatting insect, acarine or nematode pests, which comprises applying to plants or other vegetation or to the pests themselves or a location of the pest, an effective amount of one or more of the compounds according to claim 1.

12. A compound according to claim 1 in which $R^1$ is an isopropyl group, $R^2$ is a methoxymethoxy group, $R^3$ is a hydrogen atom and $OR^4$ is a hydroxy group.

* * * * *